US00PP32847P2

(12) United States Plant Patent
Jones et al.

(10) Patent No.: US PP32,847 P2
(45) Date of Patent: Feb. 23, 2021

(54) ***NEMESIA* PLANT NAMED 'SUNJON84'**

(50) Latin Name: ***Nemesia denticulata* x *caerulea***
Varietal Denomination: SUNJON84

(71) Applicant: Suntory Flowers Limited, Tokyo (JP)

(72) Inventors: David Jones, Monmouthshire (GB); Jimmy Jones, Monmouthshire (GB)

(73) Assignee: Suntory Flowers Ltd.

( * ) Notice: Subject to any disclaimer, the term of this patent is extended or adjusted under 35 U.S.C. 154(b) by 0 days.

(21) Appl. No.: 16/873,203

(22) Filed: Feb. 25, 2020

(51) Int. Cl.
*A01H 6/00* (2018.01)
*A01H 5/02* (2018.01)

(52) U.S. Cl.
USPC ..... Plt./458

(58) Field of Classification Search
USPC ..... Plt./458
CPC ..... A01H 5/02; A01H 6/00
See application file for complete search history.

*Primary Examiner* — Keith O. Robinson
(74) *Attorney, Agent, or Firm* — Cassandra Bright

(57) ABSTRACT

A new and distinct cultivar of *Nemesia* plant named 'SUNJON84' is disclosed, characterized by large bi-color flowers with a bluish-purple upper lobe and very pale purple lower lobe. Plants have a semi-upright growth habit, and prolific flowering. The new variety is a *Nemesia*, normally produced as an outdoor garden or container plant.

2 Drawing Sheets

Figure 1:
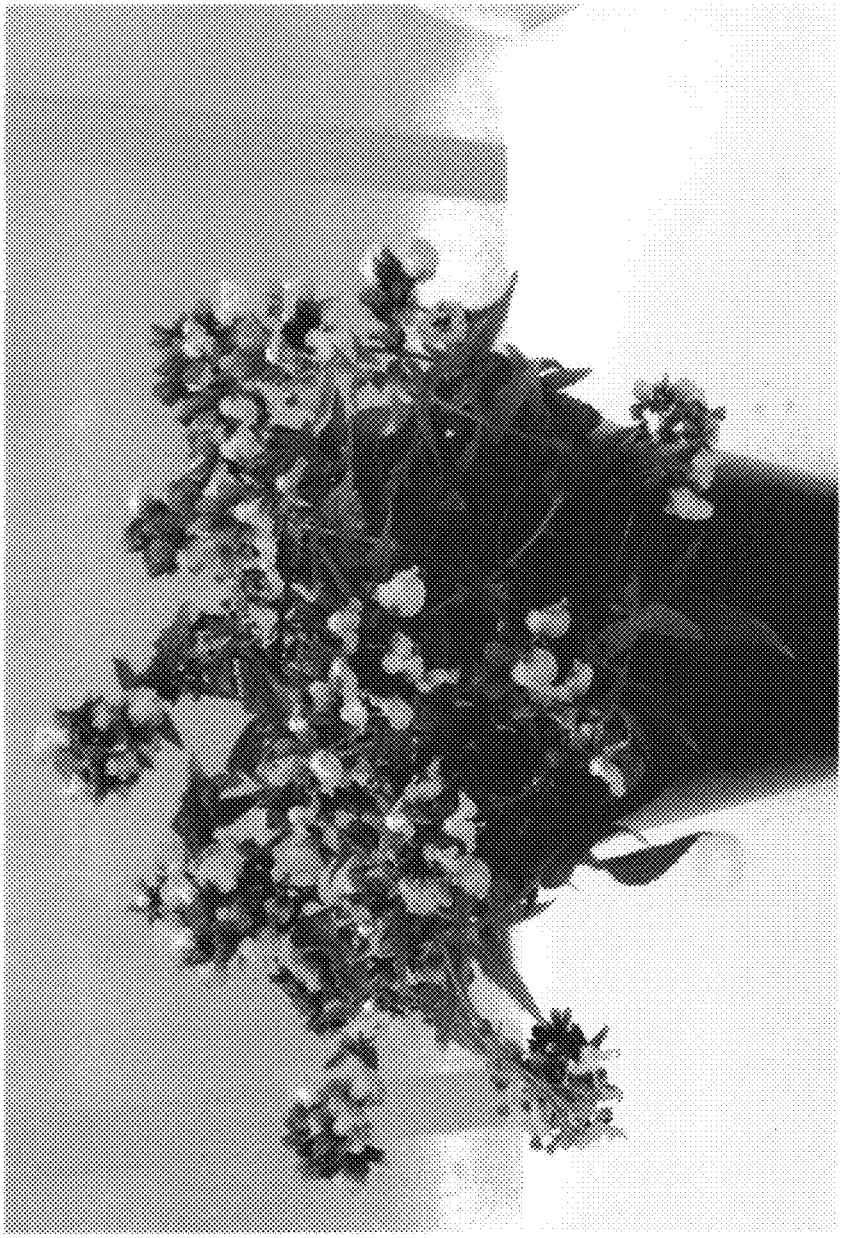

Latin name of the genus and species: *Nemesia denticulata* x *caerulea*.

Variety denomination: 'SUNJON84'.

BACKGROUND OF THE INVENTION

The new *Nemesia* cultivar is a product of a planned breeding program conducted by the inventors at a commercial greenhouse in Monmouthshire, United Kingdom. The objective of the breeding program was to produce new *Nemesia* varieties for ornamental commercial applications.

The seed parent is the unpatented proprietary seedling *Nemesia denticulata* 'A2006'. The pollen parent is the unpatented proprietary variety *Nemesia caerulea* 'A342'. The cross pollination resulting in this new variety was made during June of 2015. The new variety was found and selected during August of 2015.

Asexual reproduction of the new cultivar was performed by vegetative terminal cuttings. This was first performed at a commercial greenhouse in Monmouthshire, United Kingdom in May of 2016 and has shown that the unique features of this cultivar are stable and reproduced true to type in multiple successive generations. Date of first sale was Oct. 1, 2019, occurring in the United States. This sale was made directly by the inventor or one who obtained the claimed invention directly or indirectly from the inventor. This sale and all public disclosures made between Oct. 1, 2019 and the filing of this application fall within the exception allowed under 102(b)(1).

SUMMARY OF THE INVENTION

The cultivar 'SUNJON84' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUNJON84'. These characteristics in combination distinguish 'SUNJON84' as a new and distinct *Nemesia* cultivar:

1. Semi-upright growth habit.
2. Bi-color bluish-purple upper lobe and very pale purple lower lobe.
3. Larger flowers.
4. Longer flowering time.

PARENT COMPARISON

Plants of the new cultivar 'SUNJON84' are comparable to the seed parent variety in most horticultural characteristics; however, the new variety 'SUNJON84' differs in the following:

1. The new variety produces more inflorescences per plant than the seed parent.

Plants of the new cultivar 'SUNJON84' are comparable to the pollen parent variety in most horticultural characteristics; however, the new variety 'SUNJON84' differs in the following:

1. The new variety has a larger corolla diameter than the pollen parent.

COMMERCIAL COMPARISON

Plants of the new cultivar 'SUNJON84' are comparable to the commercial variety *Nemesia* 'Sunjon 008', U.S. Plant Pat. No. 27,679. The two *Nemesia* varieties are similar in most horticultural characteristics; however, the new variety 'SUNJON84' differs in the following:

1. Shape of the lateral lobe of the new variety is obtuse, while the lateral lobe of this comparator is rounded.
2. Color of the upper lobe of the new variety is a strong violet. The same flower part in this comparator is a deep purplish-red.

3. Primary color of the lower lobe of the new variety is very pale purple. The similar flower part in this comparator is white.
4. Secondary color of the lower lobe of the new variety is strong reddish-purple. The similar flower part in this comparator is deep reddish-purple.
5. The new variety has a longer corolla than this comparator.

BRIEF DESCRIPTION OF THE PHOTOGRAPHS

The accompanying photograph in FIG. 1 illustrates in full color a close up of the inflorescence of a 4-month-old plant.

Figure 2:
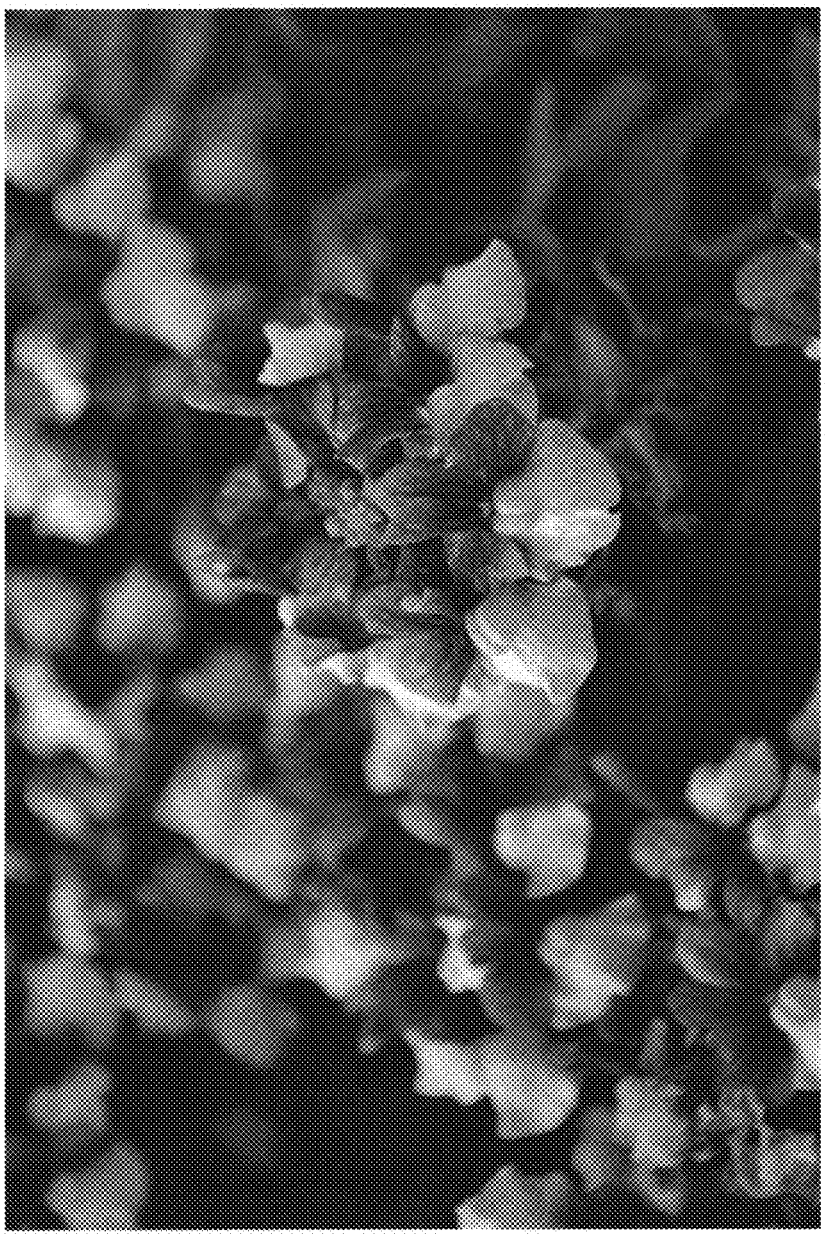

FIG. 2 illustrates a close-up view of flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SUNJON84' plants at 4 months of age grown during March of 2019, outdoors in Higashiomi, Japan. The growing temperature ranged from an average of 15° C. during the day to 5° C. during the night. General light conditions are bright, normal sunlight. Measurements and numerical values represent averages of typical plant types.

Botanical classification: *Nemesia denticulata* x *caerulea* 'SUNJON84'.

PROPAGATION

Typical method: Terminal vegetative cuttings.

Time to initiate roots: About 14 days at approximately 18° C.

Root description: Moderately dense, fibrous, freely branching. White in color, not accurately measured with R.H.S. chart.

Time to produce a rooted cutting: About 21 days at 18° C.

PLANT

Growth habit: Semi-upright tender perennial.

Pot size of plant described: 10.5 cm.

Height: Approximately 16 cm.

Plant spread: Approximately 33.5 cm.

Plant vigor: Vigorous.

Branching characteristics: Free-branching.

Length of primary lateral branches: Approximately 15 cm.

Diameter of lateral branches: Approximately 2.5 mm.

Quantity of lateral branches: Moderate branching, about 12 main laterals.

Internode length: 20.5 mm.

Stem:

*Color*.—RHS Green 138A.

*Texture*.—Smooth, glabrous.

Age of plant described: Approximately 4 months.

FOLIAGE

Leaf:

*Arrangement*.—Opposite, single.

*Quantity*.—Approximately 13 per main branch.

*Average length*.—Approximately 47.4 cm.

*Average width*.—Approximately 22.5 cm.

*Shape of blade*.—Lanceolate.

*Apex*.—Acute.

*Base*.—Broad.

*Margin*.—Shallow crenate.

*Texture of top surface*.—Smooth, glabrous.

*Texture of bottom surface*.—Smooth, glabrous.

*Variegation*.—None.

*Color*.—Young foliage upper side: RHS Green 143A. Young foliage under side: RHS Green 138B. Mature foliage upper side: RHS Green 137A. Mature foliage under side: RHS Green 137C.

*Venation*.—Type: Pinnate. Venation color upper side: RHS Green N137A. Venation color under side: RHS Yellow-Green 144A.

*Petiole*.—Average Length: Approximately 5.9 mm. Diameter: Approximately 3.1 mm. Color: RHS Yellow-Green 144A. Texture: Smooth, glabrous.

*Stipule*.—Length: 4.7 mm. Width: 2.2 mm. Color: RHS Green 138A.

FLOWER

Natural flowering season: Early Spring to early Summer.

Inflorescence type and habit: Terminal raceme.

Flower longevity on plant: 5 to 7 days.

Quantity of inflorescences per plant: 16.

Quantity of flowers per inflorescence: 11.

Inflorescence size:

*Diameter*.—Approximately 3.3 cm.

*Height*.—Approximately 4.2 cm.

Corolla:

*Shape*.—Zygomorphic.

*Length*.—Approximately 20.6 mm.

*Width*.—Approximately 15.8 mm.

*Depth*.—Approximately 15.8 mm.

*Aspect*.—Upright to outward.

*Persistence*.—Self-cleaning.

*Fragrance*.—Moderately strong, typical sweet *Nemesia* scent.

*Color change with age*.—Little to no change.

*Spur length*.—About 4 mm.

Petals:

*Arrangement*.—Bilabiate, 4 upper lobes and a lower lobe.

*Number*.—5.

*Texture*.—Smooth, upper and under sides.

*Upper lobes*.—Shape: 4 elliptic lobes fused at the base. Length: Upper: 5.2 mm. Central: 10.8 mm. Lateral: 8.9 mm. Width: Upper: 13.9 mm. Central: 4.3 mm. Lateral: 6.7 mm. Apex: Upper: Rounded. Central: Rounded. Lateral: Obtuse. Margin: Upper: Entire. Central: Entire. Lateral: Entire. Color: When opening: Upper surface: RHS Purple N78C. Lower surface: RHS Purple 77C. Fully opened: Upper surface: RHS Purple N87B. Lower surface: RHS Purple N87B. Basal Blotch: RHS Green-Yellow 7C.

*Lower lobe*.—Length: 10.3 mm. Width: 13.6 mm. Shape: Obcordate. Apex: Emarginate. Margin: Undulate. Undulation: Weak. Incision of margin: Weak. Incurving: Absent or weak. Curvature in cross section: Strong. Color: When opening: Upper surface: RHS Green-Yellow 3B. Lower surface: RHS Purple 75D. Fully opened: Upper surface: RHS Green-Yellow 3B. Lower surface: RHS Purple 75D.

*Palate*.—Size relative to lower lobe: Small. Color: Near RHS Yellow 5B.

Bud:

*Shape*.—Globular.

*Length*.—5 mm.

*Diameter*.—4.7 mm.

*Color*.—Near RHS Purple N81D.

Calyx: Star shaped, composed of 5 sepals fused at base.

Sepals:

*Shape*.—Ensiform.

*Apex*.—Acute.

*Margin*.—Entire.

*Texture*.—Smooth, upper and lower surfaces.

*Pubescence*.—Glabrous.

*Color*.—Near RHS 137C, upper and lower surfaces.

Peduncle:

*Length*.—Average 48 mm.

*Diameter*.—1.5 mm.

*Color*.—RHS Green 139B.

*Orientation*.—Upright.

*Pubescence*.—Glabrous.

*Texture*.—Smooth.

Pedicel:

*Length*.—Average 8.3 mm.

*Diameter*.—0.1 mm.

*Color*.—Near RHS Green 137C.

*Orientation*.—Upright to outward.

*Pubescence*.—Glabrous.

*Texture*.—Smooth.

REPRODUCTIVE ORGANS

Stamens:

*Number*.—4.

*Filament length* (*longer*).—About 2.1 mm.

*Filament length* (*shorter*).—About 0.9 mm.

Anthers:

*Shape*.—Ellipsoidal.

*Length*.—About 1 mm.

*Width*.—About 0.5 mm.

*Color*.—Near RHS Yellow 12A.

*Pollen*.—Moderate.

*Pollen color*.—Near RHS White 155A.

Pistil:

*Number*.—1.

*Length*.—About 4 mm.

*Style*.—Length: About 1 mm. Color: Near RHS White 155C.

*Stigma*.—Shape: Ovoid. Color: Near RHS White 155C. Ovary color: Near RHS Green 137C.

OTHER CHARACTERISTICS

Seeds and fruits: Seed and fruit production has not been observed.

Disease/pest resistance: Neither resistance nor susceptibility observed. Typical diseases include *Pythium* and *Phytopthera*. Various species of White Fly, Aphis and Mites may infect *Nemesia*.

Temperature tolerance: Typically tolerant of temperatures from 5° C. to 35° C. Perennial in USDA Zones 9 and 10.

What is claimed is:

1. A new and distinct cultivar of *Nemesia* plant named 'SUNJON84' as herein illustrated and described.

* * * * *